United States Patent [19]

Terui et al.

[11] 4,105,804

[45] Aug. 8, 1978

[54] METHOD FOR SEPARATION OF BACTERIA CELLS FROM CULTURE BROTH

[75] Inventors: Gyozo Terui, 8-26, Tanabe-Nishinocho, Higashisumiyoshi-ku, Osaka; Nobuo Takada, Neyagawa; Shuzo Sawada, Tokyo, all of Japan

[73] Assignee: Gyozo Terui, Osaka, Japan

[21] Appl. No.: 668,528

[22] Filed: Mar. 19, 1976

Related U.S. Application Data

[63] Continuation-in-part of Ser. No. 544,649, Jan. 27, 1975, abandoned, which is a continuation-in-part of Ser. No. 437,726, Jan. 30, 1974, abandoned.

[30] Foreign Application Priority Data

Jan. 31, 1973 [JP] Japan .................................. 48/13116

[51] Int. Cl.$^2$ ................................................ A23J 1/00
[52] U.S. Cl. ........................................ 426/656; 195/29; 426/61; 426/657
[58] Field of Search ................................ 426/656, 657; 260/112 R, 119, 120; 195/4, 29, 105, 106; 210/42, 45, 54

[56] References Cited

U.S. PATENT DOCUMENTS

| | | | |
|---|---|---|---|
| 2,251,334 | 8/1941 | Hall | 426/580 X |
| 2,548,520 | 2/1947 | Damschroder et al. | 260/112 R X |
| 3,356,507 | 12/1967 | Wingerd | 260/112 R X |
| 3,583,968 | 6/1971 | Pien | 260/112 R |
| 3,681,283 | 8/1972 | Yueh | 260/112 R X |
| 3,778,514 | 12/1973 | Olson | 426/657 X |

*Primary Examiner*—R. B. Penland
*Attorney, Agent, or Firm*—Birch, Stewart, Kolasch and Birch

[57] ABSTRACT

Bacterial cells are separated from a culture broth by adding thereto a solution of casein or alkali-soluble soybean proteins, said culture broth being maintained at a pH less than 6. Bacteria cells are flocculated to form a protein-bacteria co-precipitate which is easily separable by a conventional procedure. The co-precipitate may be directly put to uses such as for foods or feeds.

6 Claims, 7 Drawing Figures

METHOD FOR SEPARATION OF BACTERIA CELLS FROM CULTURE BROTH

This application is a continuation-in-part of our prior U.S. application Ser. No. 544,649 filed Jan. 27, 1975 which is a continuation-in-part of U.S. application Ser. No. 437,726, filed Jan. 30, 1974 both now abandoned.

This invention relates to a method for separating bacteria cells from a culture broth containing the same.

As is well known, the separation of bacteria cells from a culture broth containing the same by means of conventional procedures such as filtration is generally difficult. This is not seen in separation of the other microorganisms. Accordingly, the production of bacteria cells on an economical scale has been greatly hindered. Heretofore, there has been known as a means for sewage treatment a method for flocculating bacterial cells by the addition of metal salts and the like. However, the application of metal salts to foods or feeds could cause unexpected problems in food sanitation. Accordingly, this method is undesirable from the standpoint of pollution.

The object of the present invention is to provide a quick and safe method for the separation of bacteria cells from a culture broth.

In accordance with the present invention, a solution of casein or alkali-soluble soybean protein is added to a culture broth containing bacteria cells at a pH less than 6, thereby flocculating and co-precipitating the bacteria cells. Control of the pH may be effected either before or after the addition of the solution of casein or alkali-soluble soybean protein.

The method of the present invention can be applied to so called "bacteria", for example, *Escherichia coli, Bacillus subtilis, Pseudomonas methanolica, Aerobacter aerogenes, Micrococcus flavus, Serratia marcescens* or *Bacillus cereus.*

Casein to be used in the invention is soybean or animal milk casein or alkali-soluble soybean proteins. Ordinarily, soybean protein extract, for example, is prepared by extraction of soybean with 0.05 to 5 N NaOH at 20° to 100° C for 5 minutes to 6 hours.

The pH of the culture broth is controlled to below 6. The preferred pH depends on the casein to be added; for example 1.8 to 5.0, particularly 2.5, for soybean casein, and 4.0 - 5.0, particularly 4.7, for milk casein. When the bacteria is cultured on a solid medium, the cells have to be separated from the medium to prepare a suspension, before the pH is controlled. There are some cases where almost complete precipitation or flocculation of bacteria cells occurs only after the pH is controlled to 1.5 to 3.5 without addition of casein, depending on the bacteria, especially *Escherichia coli* or *Bacillus subtilis.* Any acid can be used for controlling the pH, as long as it is not harmful to animals, preferably hydrochloric acid. It is not critical when the control of the pH is effected. In other words control of the pH is effected either before or after the casein or soybean protein is added.

The amount of bacteria cells precipitated increases as the soybean protein or casein is added.

In the accompanying drawings.

The present invention is further explained by reference to the following Examples, which are shown only for illustrative purposes.

EXAMPLE 1

| Preparation of culture broth | |
|---|---|
| Medium composition: | |
| KH$_2$PO$_4$ | 0.5 g |
| (NH$_4$)$_2$HPO$_4$ | 2.0 g |
| KCl | 0.1 g |
| MgSO$_4$ . 7H$_2$O | 0.2 g |
| FeSO$_4$ . 7H$_2$O | 0.01 g |
| Methanol | 2.0 g |
| Water | 1 liter |

Figure 1A:
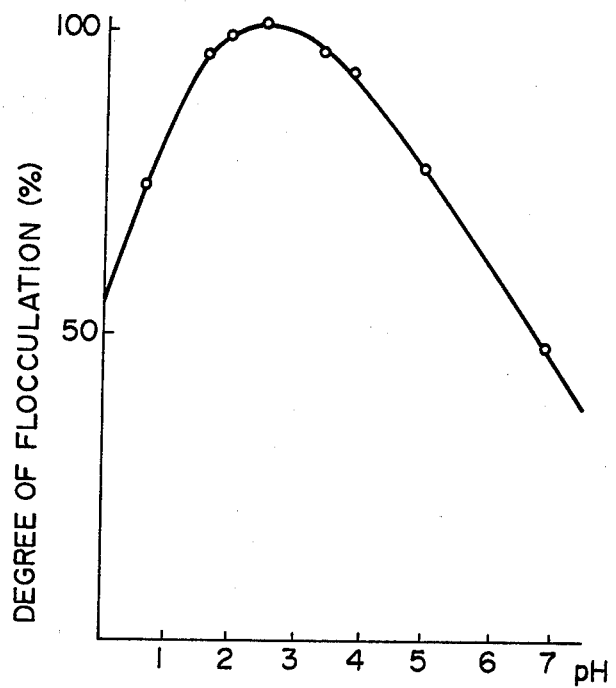
FIG. 1a shows a diagram denoting the variation in degree of precipitation according to pH value when a *Pseudomonas methanolica* culture broth is adjusted to various pH values and 0.2 g of soybean casein (alkali-soluble acid precipitable protein from soybeans) dissolved in 10 ml of 0.1 N NaOH solution is added per *l* of the culture broth containing 5 g (dry weight) of bacteria cells.
Figure 1B:
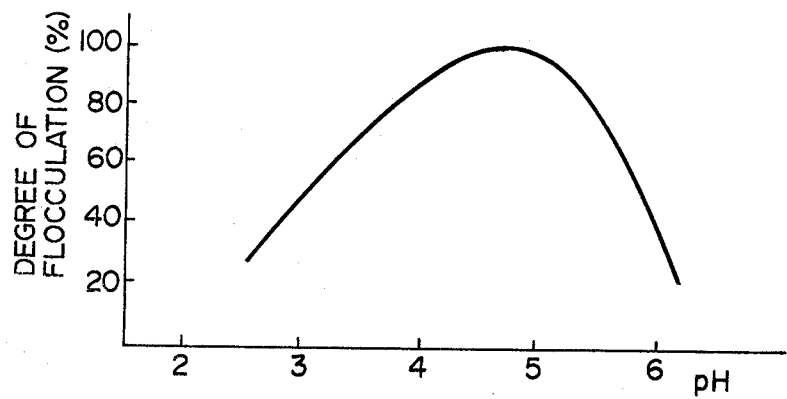
FIG. 1b shows a diagram denoting the relation between pH and the degree of precipitation when 1 liter of *Pseudomonas methanolica* culture broth is adjusted to various pH values and 0.2 g of milk casein (dissolved in 10 ml of 0.1 N NaOH solution) is added to the broth.
Figure 2A:
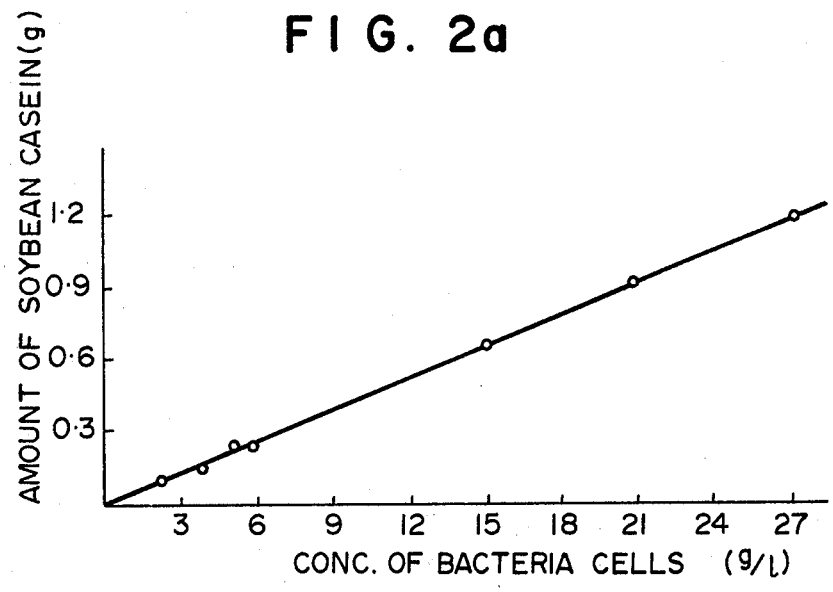
FIG. 2a shows the relationship between the amount of soybean casein needed for precipitation (99% or more) and the concentration of the bacteria cells in the culture broth at pH 2.5, in connection with *Pseudomonas methanolica.*

Fifty ml of a liquid medium having the above composition is charged into a 500 ml Erlenmeyer flask. This medium is then inoculated with the methanol utilizing bacterium of *Pseudomonas methanolica* and culturing is conducted at 30° C by means of a 100 r.p.m. rotary shaker, with 2 g of methanol per liter of culture broth being added four times. After about 12 hours, an approximately maximum concentration of the bacteria is obtained. To the culture broth is added soybean casein treated with five fold by weight of 0.1 N NaOH aqueous solution at 60° C for 1 hour and then the pH is adjusted by 1 N hydrochloric acid to 2.5. The amount of bacteria cells precipitated is increased according to the amount of soybean casein added as shown in FIG. 2a.

EXAMPLE 2

Figure 2B:
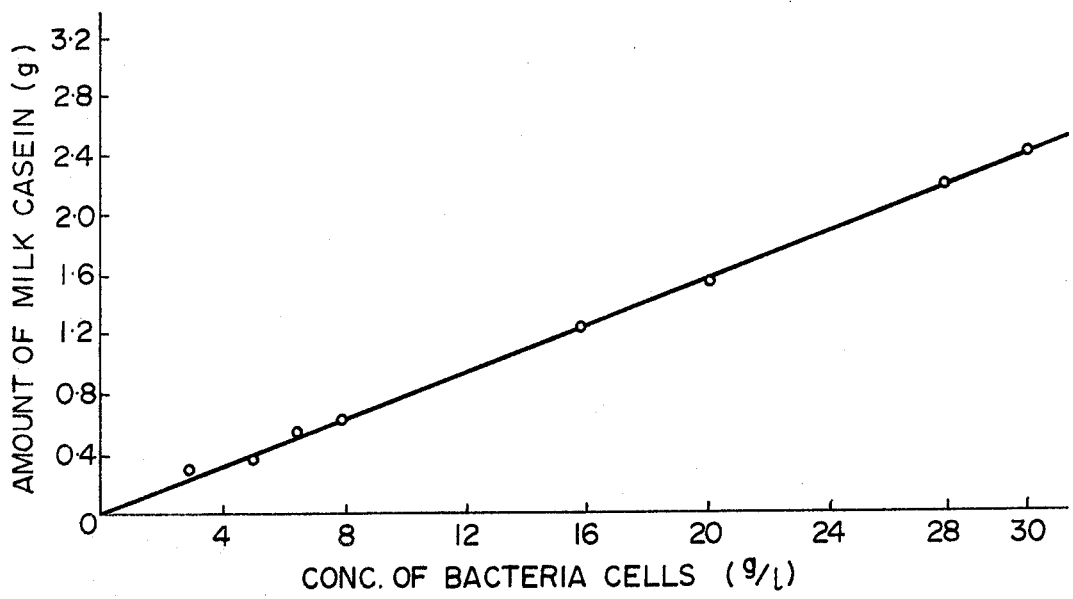
FIG. 2b shows the relationship between the amount of milk casein needed for precipitation (99% or more) and the bacterial cell concentration in the same culture broth as FIG. 2a. The pH value is adjusted to 4.7.

Example 1 is repeated except the pH is controlled at 4.7 and milk casein is added in place of soybean casein. The amount of bacteria cells precipitated is increased according to the amount of milk casein added as shown in FIG. 2b. In the above experiment, the cell concentration is controlled either by diluting with culture centrifugate or by concentrating through centrifugation.

Figure 2C:
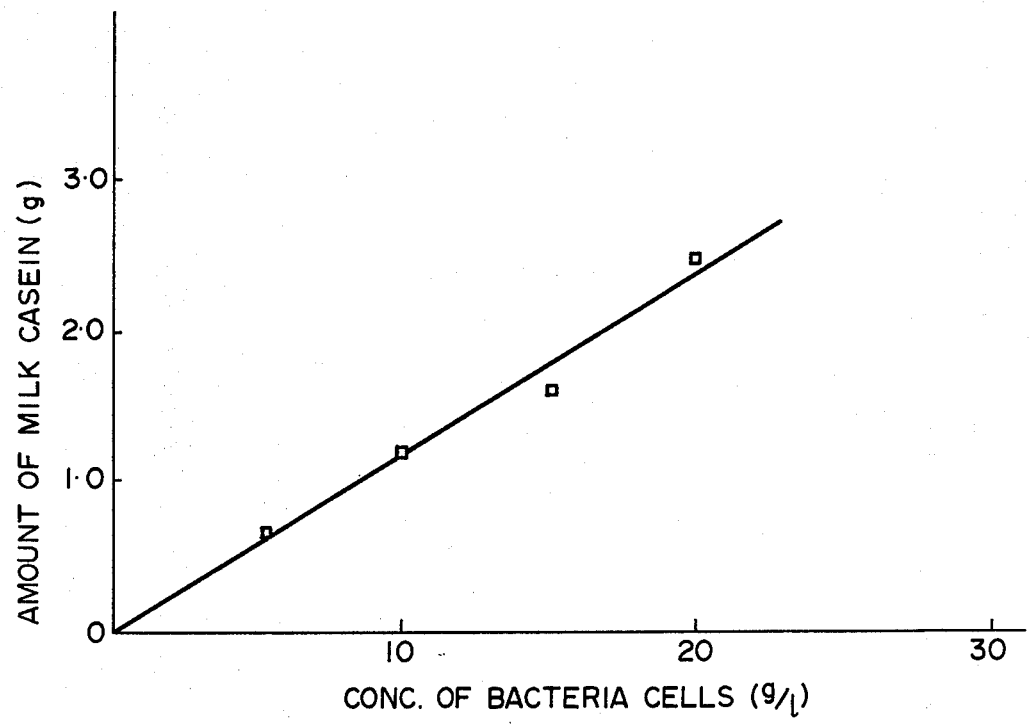
FIG. 2c shows the relation between the amount of milk casein needed for precipitation (99% or more) and the bacterial cell concentration of *Escherichia coli* at pH 4.7.

The experiment above is repeated except *Escherichia coli* cells are used in place of *Pseudomonas methanolica* cells, as shown in FIG. 2c.

EXAMPLE 3

Figure 3:
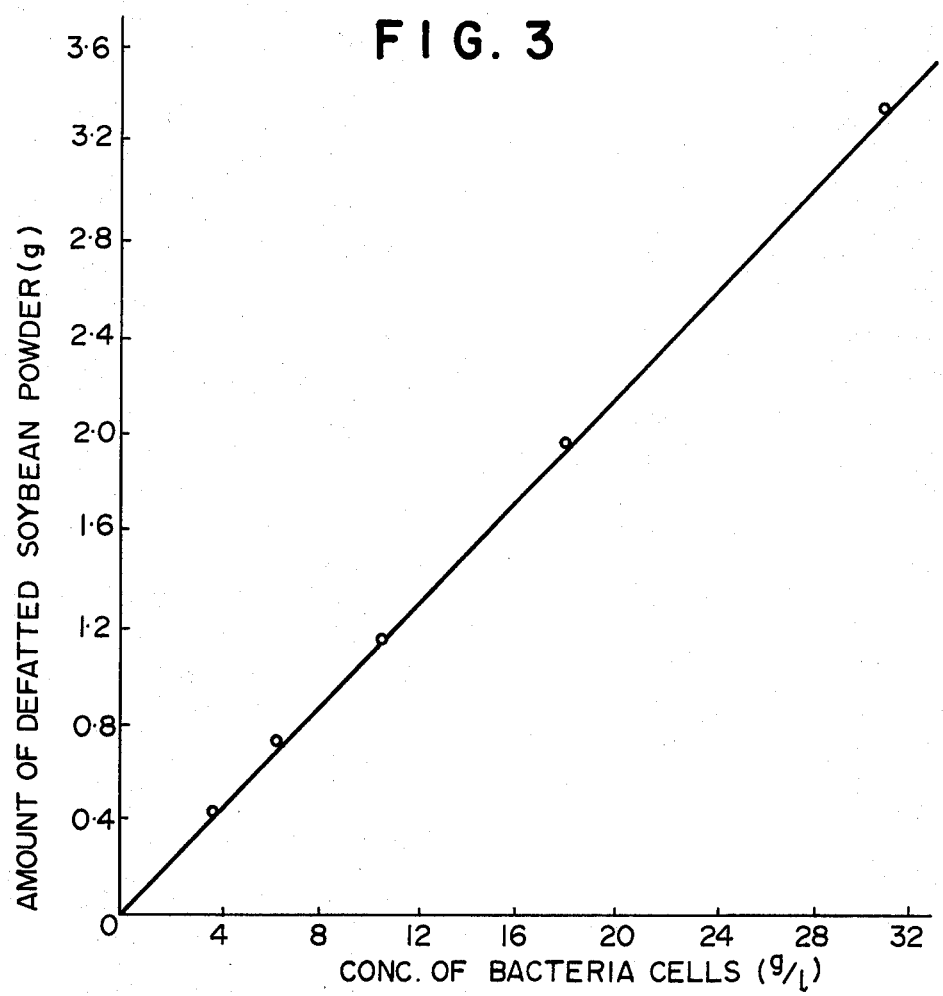
FIG. 3 shows the relationship between the amount of defatted soybean powder (one gram of defatted soybean protein corresponds to about 0.4 g of soybean casein in the extract) needed for precipitating cells of *Pseudomonas methanolica* (99% or more) and the concentration of the bacteria cells of said bacteria.

Example 1 is repeated except that defatted soybean powder as described below is used in place of the soybean casein. The soybean powder is prepared by extraction of defatted soybean with 0.1 N NaOH aqueous solution (10 times the weight of defatted soybean powder) at 60° C for 1 hour, followed by filtration. The amount of bacteria cells precipitated increases in relation to the amount of defatted soybean powder added as shown in FIG. 3.

EXAMPLE 4

To 1 liter of broth containing 16 g of *Pseudomonas methanolica* obtained by a continuous culture method is added a soybean protein extract solution (prepared by extracting 1.8 g of defatted soybean powder with 18 ml of 0.1 N NaOH solution at 60° C for 1 hour, followed by filtration) and then the pH is adjusted to 2.5 to complete co-precipitation. The co-precipitate is separated by filtration at room temperature, washed with water and dried at 105° C under normal pressure for 6 hours to obtain 15.5 g of dry bacteria cells. A small amount of loss is incurred during operation in this case. From the result of amino acid analysis, the product is found to be of high nutritive value suitable as fodder for chickens or hogs. Said dry bacteria cells are hydrolyzed with 10 N sulfuric acid for one to two days and the hydrolyzed product is analyzed with an amino acid automatic analyzer (Hitachi Seisakusho Co; KLA-3B) to determine the quantities of amino acids, only tryptophan being determined by the Xanthydrol method (J. Biol. Chem. 220, 957, 1956). The result is shown in the following Table, from which it is estimated that the dry cells are of high nutritive value.

| Amino acid content (%) | |
|---|---|
| Lysine | 3.4 |
| Hystidine | 1.3 |
| Alginine | 3.8 |
| Asparagine | 9.4 |
| Threonine | 4.1 |
| Serine | 3.6 |
| Glutamine | 10.0 |
| Proline | 5.1 |
| Glycine | 4.2 |
| Alanine | 5.6 |
| Valine | 4.4 |
| Methionine | 1.3 |
| Isoleucine | 3.9 |
| Leucine | 5.9 |
| Tyrosine | 2.4 |
| Phenylalanine | 3.4 |
| Tryptophane | 0.6 |
| Cystine | 0.3 |

EXAMPLES 5 – 10

Figure 4:
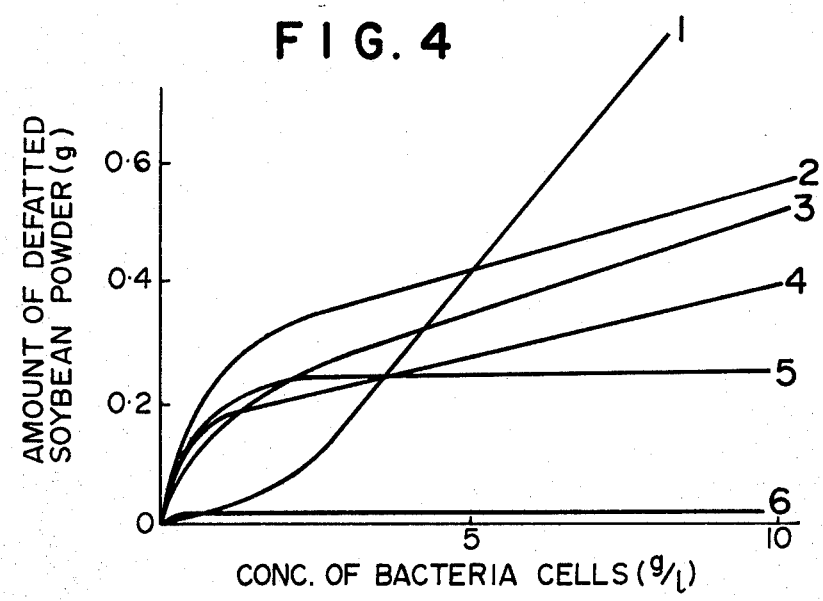
FIG. 4 shows the relationship between the amounts of defatted soybean powder needed for 99% or more precipitation and the concentration of bacteria cells in the culture broth with *Aerobacter aerogenes, Micrococcus flavus, Serratia marcescens, Bacillus cereus, Escherichia coli* and *Bacillus subtilis.*

Various bacteria, namely (1) *Aerobacter aerogenes*, (2) *Micrococcus flavus*, (3) *Serratia marcescens*, (4) *Bacillus cereus*, (5) *Escherichia coli* and (6) *Bacillus subtilis* (as shown by the respective curves in FIG. 4) are used. These bacteria are respectively cultured in a medium (pH 7.0) containing 0.3% meat extract and 0.5% peptone by means of a 100 r.p.m. rotary shaker at 30° C for 18 hours. Each culture broth is adjusted to pH 2.5 and thereafter a soybean protein extract solution, which is prepared by extraction with 0.1 N NaOH solution (10 times the weight of defatted soybean powder) at 60° C for 1 hour, followed by filtration, is added thereto. The amounts of bacteria cells precipitated are shown in FIG. 4. Even for higher concentrations of, for example, *Aerobacter aerogenes* cells, extrapolation of the linear part of the curve 1 is valid. The experimental result with a cell concentration of 27 g/l of *Aerobacter aerogenes* indicates that the amount of defatted soybean powder for obtaining a clear supernatant is 3.1 – 3.4 g per liter.

The microorganisms used in the above examples are *Pseudomonas methanolica* ATCC 21704, *Aerobacter aerogenes* OUT 8017, *Micrococcus flavus* OUT 8276, *Serratia marcescens* OUT 8259, *Bacillus cereus* OUT 8032, *Escherichia coli* OUT 8278, and *Bacillus subtilis* OUT 8038.

What we claim is:

1. A method for separating bacteria cells from a culture broth, which comprises adjusting the pH of said culture broth in the form of a suspension to less than 6 and adding thereto, before or after pH adjustment, a sufficient amount of a solution of casein or alkali-soluble soybean proteins to precipitate the bacteria cells.

2. A method according to claim 1 wherein the casein is soybean casein or milk casein.

3. A method according to claim 1 wherein the pH is controlled within the range of 1.8 to 5.0 and soybean casein is added to the broth.

4. A method according to claim 3 wherein the pH is 2.5.

5. A method according to claim 1 wherein the pH is controlled within the range of 4.0 to 5.0 and milk casein is added to the broth.

6. A method according to claim 5 wherein the pH is 4.7.

* * * * *